United States Patent
Hamilton

(10) Patent No.: US 7,811,971 B2
(45) Date of Patent: Oct. 12, 2010

(54) COMBINATION ALGAE KILLER AND SURFACE STAIN REMOVER

(75) Inventor: Scott Hamilton, Santa Paula, CA (US)

(73) Assignee: United Chemical Corp., Piru, CA (US)

( * ) Notice: Subject to any disclaimer, the term of this patent is extended or adjusted under 35 U.S.C. 154(b) by 204 days.

(21) Appl. No.: 11/951,469

(22) Filed: Dec. 6, 2007

(65) Prior Publication Data

US 2009/0149327 A1 Jun. 11, 2009

(51) Int. Cl.
*A01N 59/00* (2006.01)
*C11D 3/395* (2006.01)

(52) U.S. Cl. ...................... 504/119; 510/199
(58) Field of Classification Search .............. 504/119; 510/199
See application file for complete search history.

(56) References Cited

U.S. PATENT DOCUMENTS

| | | | |
|---|---|---|---|
| 4,067,808 A | 1/1978 | Phillips | |
| 4,256,599 A | 3/1981 | Krisp et al. | |
| 4,361,471 A | 11/1982 | Kosarek | |
| 4,755,354 A | 7/1988 | Trinh et al. | |
| 4,906,384 A | 3/1990 | Hamilton | |
| 5,071,569 A | 12/1991 | Caulfield et al. | |
| 5,130,033 A | 7/1992 | Thornhill | |
| 6,120,698 A * | 9/2000 | Rounds et al. | 252/181 |
| 6,562,243 B2 | 5/2003 | Sherman | |
| 6,660,307 B2 | 12/2003 | Zolotarsky et al. | |
| 6,827,847 B1 | 12/2004 | Chauvier | |
| 7,195,782 B2 | 3/2007 | Moore et al. | |
| 2009/0206298 A1* | 8/2009 | Hamilton | 252/175 |

FOREIGN PATENT DOCUMENTS

WO  WO 99/62339  * 12/1999
WO  WO 2007/023481  * 3/2007

* cited by examiner

*Primary Examiner*—Johann R Richter
*Assistant Examiner*—Danielle Sullivan
(74) *Attorney, Agent, or Firm*—Fish & Associates, PC

(57) ABSTRACT

A stain removal formula includes a combination of a bromide donor, a salt of sulfamic acid; and a salt of phosphoric acid. Preferred formulas include effective amounts of sodium bromide, sodium sulfamic acid, sodium hexametaphosphate, disodium phosphate, and tetrasodium pyrophosphate. In a swimming pool, preferred formulas are effective in resolving algae stain within a 2 hour period, which represents at least an order of magnitude greater efficacy than prior art formulations. In addition, preferred formulas provide ongoing effectiveness in suppressing bacterial, fungal and/or algae growth.

13 Claims, 1 Drawing Sheet

COMBINATION ALGAE KILLER AND SURFACE STAIN REMOVER

FIELD OF THE INVENTION

The field of the invention is cleansing swimming pools.

BACKGROUND

The water in swimming pools is often contaminated by foreign substances, including for example, tree branches, leaves, bacteria, and fungus. Such contamination can stain the side walls and other surfaces of the pools, and such stains can be quite difficult to remove.

U.S. Pat. No. 4,906,384 to Hamilton (Mar. 6, 1990) teaches the use of acids to remove scale deposits and stains from the sides of swimming pools, and U.S. Pat. No. 5,071,569 to Caulfield et al. (Dec. 10, 1991) teaches the use of EDTA compounds and ammonium ions to removing algae stains. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Some formulas combine stain removing compositions with sanitizing compositions. For example U.S. Pat. No. 6,562,243 to Sherman (May 13, 2003) teaches a formula that combines oxidizing agents (chlorine) with algaecides. Unfortunately, the level of chlorine that is appropriate for a swimming pool can take days or even weeks to provide adequate stain removal. The problem is compounded because different swimming pool chemicals can interfere with each other. An addition of too much sodium bromide to a swimming pool, for example, can destabilize chlorine, requiring an even greater addition of chlorine to cleanse the pool.

Thus, there is still a need for swimming pool chemical formulas that provide both rapid stain removal and effective antimicrobial action.

SUMMARY OF THE INVENTION

The present invention provides systems, compositions and methods in which a stain removal formula includes a combination of a bromide donor, a salt of sulfamic acid; and a salt of phosphoric acid.

Preferred formulas include effective amounts of sodium bromide, sodium sulfamic acid, sodium hexametaphosphate, disodium phosphate, and tetrasodium pyrophosphate. Experimental work has demonstrated that the dry weight ratio between sodium bromide and sodium sulfamic acid should be at least 3:1. Especially preferred formulas include at most 70 wt % sodium bromide, at least 20 wt % sulfamic acid, at least 5 wt % sodium hexametaphosphate, at least 0.5 wt % tetrasodium pyrophosphate, and at least 0.5 wt % disodium phosphate.

As used herein, the term "salt" includes the dry form and a solvated form. Thus, a claim to "a solution for treating water in a swimming pool, comprising: a bromide donor; a salt of sulfamic acid; and a salt of phosphoric acid" should be interpreted to mean a liquid form in which all three salts are at least partially solvated.

In a swimming pool, preferred formulas are effective in resolving algae stain within a 2 hour period, which represents at least an order of magnitude greater efficacy than prior art formulations. In addition, preferred formulas provide ongoing effectiveness in suppressing bacterial, fungal and/or algae growth.

Preferred formulas can be introduced into a swimming pool in a variety of ways, including addition of liquid and/or solid forms. In addition, components of the formulas can be added separately to the pool, or can be combined and added together in solid or liquid form.

Those skilled in the art will appreciate that the principles taught herein can be readily applied to other applications besides swimming pools. Of particular interest are applications having re-circulating or stagnant water, including for example, decorative ponds, water fountains and toilets.

Various objects, features, aspects and advantages of the inventive subject matter will become more apparent from the following detailed description of preferred embodiments.

DETAILED DESCRIPTION

Figure 1:
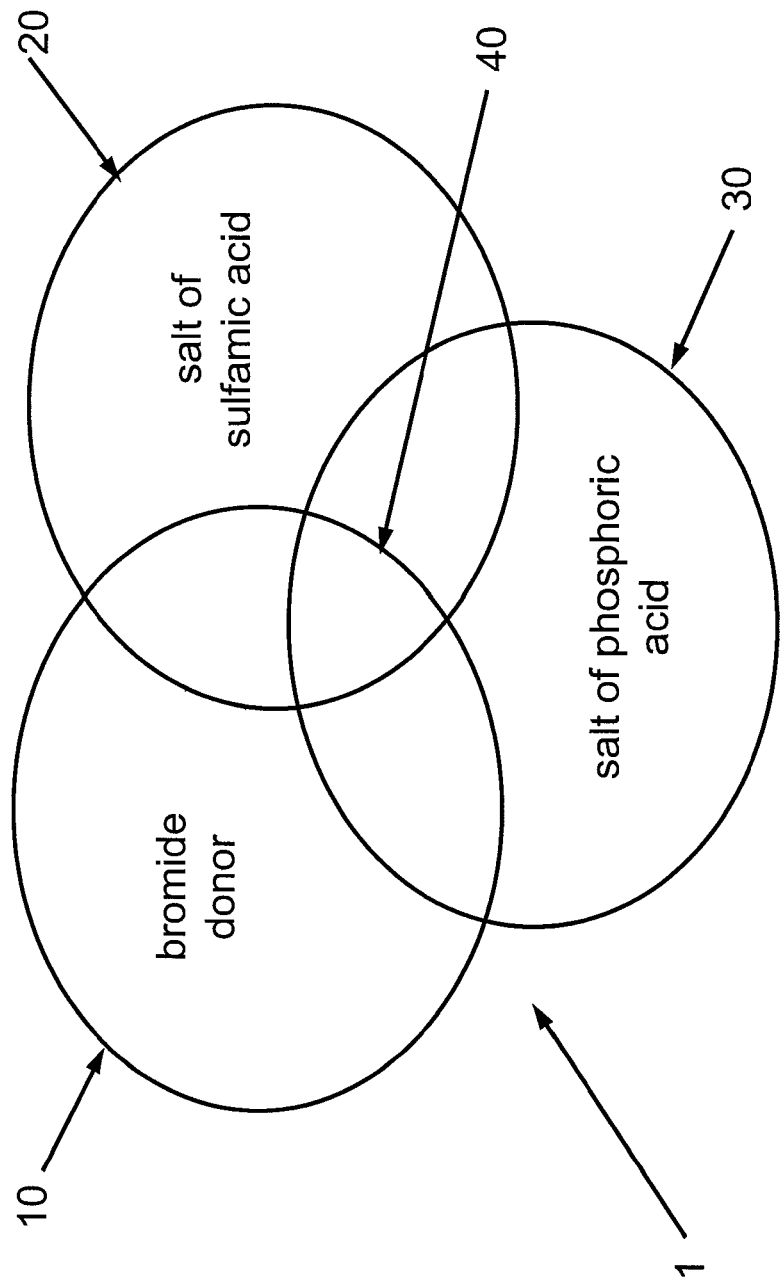
FIG. 1 is a schematic of a preferred anti-stain formulation.

FIG. 1 generally shows a Venn diagram 1 having circles that correspond to sets for a bromide donor 10, a salt of a sulfamic acid 20, and a salt of a phosphoric acid 30. The intersection of the three sets 10, 20, 30 is a set of preferred formulations 40.

The bromide donor of set 10 can be any suitable bromide donor that oxidizes to a biocide when added to water, including for example, potassium bromide, lithium bromide, sodium bromide, and hydrobromic acid. Most preferably, the bromide donor is sodium bromide (NaBr).

The effective amount of the bromide donor, when dispersed in a swimming pool or other vessel, is that amount necessary to substantially suppress algae growth, when used in combination with the other components of the formula. In preferred formulas, the dry weight ratio between the bromide donor and the sulfamic acid salt is at least 3:1. The dry weight percent of the bromide donor in preferred formulas is less than 90 wt %, more preferably less than 80 wt %, and most preferably less than 70 wt %.

The addition of the sulfamic acid and phosphoric acid salts not only decreases the necessary effective wt % of sodium bromide in the solution, but also dissolves stain deposits in the liquid container. The effective amounts of the sulfamic acid and phosphoric acid salts, when dispersed in a swimming pool or other vessel, is that amount necessary to reduce an algae stain on a wall of the vessel by at least 50% within 2 hours of application.

The salt of sulfamic acid can be any suitable sulfamic acid, for example potassium sulfamic acid, phenyl sulfamic acid, ammonium sulfamic acid, or sodium sulfamic acid. The salt of sulfamic acid is preferably sodium sulfamic acid ($H_2NSO_3H$), and more preferably comprises over 10 or 20 wt % of the solution.

Likewise, the salt of phosphoric acid can be any suitable phosphoric acid, for example sodium hexametaphosphate ($Na_2OP_2O_5$), disodium phosphate, or tetrasodium pyrophosphate. Here, however, the phosphoric acid is preferably produced in solution by a combination of multiple salts of phosphoric acid. The total wt % of the salts of phosphoric acid can be relatively small, but is preferably greater than 5 wt % of the solution. When combining multiple salts of phosphoric acid, sodium hexametaphosphate preferably comprises a larger wt % than the others.

Especially preferred formulas include at most 70 wt % sodium bromide, at least 20 wt % sulfamic acid, at least 5 wt % sodium hexametaphosphate, at least 0.5 wt % tetrasodium pyrophosphate, and at least 0.5 wt % disodium phosphate.

At present, the most preferred embodiment comprises 67.5% sodium bromide, 22.5% sodium sulfamic, 6.5% sodium hexametaphosphate, 2.1% disodium phosphate, and 1.4% tetrasodium pyrophosphate. A gallon of this embodiment can effectively treat a 30,000 gallon pool in as little as two hours. Previous solutions of greater than 85% sodium bromide required a full day or more to kill algae growth.

The components of contemplated formulas can be mixed on-site, added individually to the swimming pool or other vessel, or can mixed and packaged in a bottle or capsule to aid in dispersing and measuring. When the components are provided separately, it is preferred that a ratio is enforced between or among the different components. Examples of enforcing a ratio include selling individual components with accompanying instructions regarding preferred ratios, providing a website that includes such instructions, or providing a measuring device in a package with the components.

A ratio can also be enforced between the chemical solution and the total volume of liquid in the vessel. This ratio can be maintained in any suitable manner, including for example measuring a predetermined amount of each chemical before adding the chemical to the liquid, or tracking the volume or weight of each chemical as it is pumped or otherwise added to the liquid. The chemical solution is preferably added in or around a pump or mixing device, for example a swimming pool pump, to aid in maximizing the dispersal of the chemical in the liquid container.

All suitable solid forms of the contemplated formulas are contemplated, including for example one or more dissolving tablets. All suitable liquid forms are also contemplated, including containers that provide only enough composition for a single treatment, and containers that provide enough composition for multiple treatments.

The present invention may be further understood in light of the following examples, which are illustrative in nature and are not to be considered as limiting the scope of the invention.

EXAMPLE 1

A pool pump in a 10,000 gallon test pool was turned off for 3 weeks, preventing any circulation. After 3 weeks, the pool appeared swampy and developed significant mustard algae growth and some green algae growth. Adding 8 oz of the inventive solution and one pound of shock dissolved the algae stains within 3.5 hours.

EXAMPLE 2

A 20,000 gallon white plaster pool with a water temperature of 88° F. was filled with green algae growth. One pound of the inventive solution and two pounds of calcium hypochlorite were added to the pool, and the water was backwashed twice. Within two hours, the pool was completely clear and free of algae.

EXAMPLE 3

Both black and green algae stained a 14,000 gallon white plaster pool with a water temperature of 91° F. One pound of the inventive solution and 3.5 pounds of calcium hypochlorite were added to the pool, and the water was backwashed three times. Within 24 hours, all the algae stains completely dissolved.

Thus, specific embodiments and applications of combination algae killer and surface stain removers have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A chemical composition for treating algae and algae stains, comprising:
   an effective amount of sodium bromide;
   an effective amount of sodium sulfamic acid, wherein the effective amount of sodium sulfamic acid comprises at least 20 wt % of the chemical composition; and
   an effective amount of sodium hexametaphosphate, wherein the dry weight ratio between the effective amount of sodium bromide and the effective amount of sodium sulfamic acid is at least 3:1.

2. The chemical composition of claim 1, further comprising at least 0.5 wt % disodium phosphate.

3. The chemical composition of claim 1, further comprising at least 0.5 wt % tetrasodium pyrophosphate.

4. The chemical composition of claim 1, wherein the sodium bromide comprises at most 70 wt % of the composition.

5. The chemical composition of claim 1, wherein the sodium sulfamic acid comprises at least 20 wt % of the composition.

6. The chemical composition of claim 1, wherein sodium hexametaphosphate comprises at least 5 wt % of the composition.

7. The chemical composition of claim 1, wherein the chemical composition is in liquid form.

8. The chemical composition of claim 1, wherein the effective amount of sodium bromide is 67.5 wt %.

9. The chemical composition of claim 1, wherein the effective amount of sodium sulfamic acid is 22.5 wt %.

10. The chemical composition of claim 1, wherein the effective amount of sodium hexametaphosphate is 6.5 wt %.

11. The chemical composition of claim 1, further comprising 2.1 wt % disodium phosphate.

12. The chemical composition of claim 1, further comprising 1.4 wt % tetrasodium pyrophosphate.

13. A chemical composition for treating algae and algae stains in a pool, comprising:
   67.5 wt % sodium bromide;
   22.5 wt % sodium sulfamic acid;
   6.5 wt % sodium hexametaphosphate;
   2.1 wt % disodium phosphate; and
   1.4 wt % tetrasodium pyrophosphate.

* * * * *